United States Patent [19]

Luzzio et al.

[11] Patent Number: 5,126,351

[45] Date of Patent: Jun. 30, 1992

[54] ANTITUMOR COMPOUNDS

[75] Inventors: Michael J. Luzzio; Jeffrey M. Besterman, both of Durham; Michael G. Evans, Pittsboro; M. Ross Johnson, Chapel Hill, all of N.C.;

[73] Assignee: Glaxo Inc., Research Triangle Park, N.C.

[21] Appl. No.: 645,373

[22] Filed: Jan. 24, 1991

[51] Int. Cl.$^5$ .................... C07D 215/18; A61K 31/47
[52] U.S. Cl. ...................... 514/291; 546/90; 546/153; 514/312
[58] Field of Search .......... 546/79, 153, 90; 514/290, 312, 291

[56] References Cited

U.S. PATENT DOCUMENTS 4,578,393  3/1986  Markwell et al. .......... 546/79
4,962,203  10/1990  Young et al. .......... 546/153

OTHER PUBLICATIONS

Chemical Abstracts Service: 110:8105, 1989.
Chemical Abstracts Service: 87:167845, 1977.
Chemical Abstracts Service: 99:187073, 1983.
Chemical Abstracts Service: 94:121454.
Chemical Abstracts Service: 59:9976h, 1963.
Chemical Abstracts Service: 55:27313i.

*Primary Examiner*—C. Warren Ivy
*Assistant Examiner*—Catherine S. Kilby Scalzo
*Attorney, Agent, or Firm*—Charles T. Joyner

[57] ABSTRACT

The present invention relates to the compounds of formula (I),

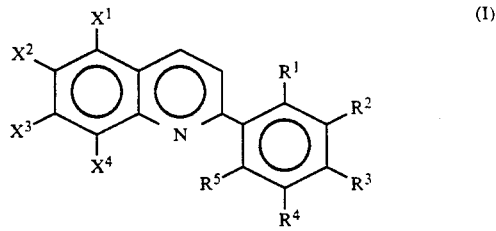

wherein:

$R^1$ is hydrogen, hydroxy or amino;
$R^2$ is hydrogen, hydroxy, methoxy or methoxymethoxy;
$R^3$ is hydrogen, hydroxy, amino, methoxy, methoxymethyoxy, or taken together with $R^2$, methylenedioxy (also known as 1,3-dioxolo);
$R^4$ is hydrogen, hydroxy, methoxy, methoxymethoxy, benzyl, di($C_{1-4}$)alkylaminomethyl or, taken together with $R^3$, methylenedioxy;
$R^5$ is hydrogen or hydroxy; provided that at least one of $R^1$ through $R^5$ is other than hydrogen; and
i) $X^2$ is hydroxy or methoxy with $X^1$, $X^3$ and $X^4$ being hydrogen; or
ii) $X^1$ taken together with $X^2$,
$X^2$ taken together with $X^3$ or $X^3$ taken together with $X^4$, is methylenedioxy, provided that each of the remaining respective $X^1$, $X^2$, $X^3$ and $X^4$ substituents are hydrogen, intermediates in the synthesis of them, pharmaceutical formulation containing them, their use as inhibitors of topoisomerase and their use in the treatment of tumors.

16 Claims, No Drawings

ANTITUMOR COMPOUNDS

The present invention relates to certain substituted phenylquinoline derivatives which have topoisomerase inhibition and antitumor activity.

BACKGROUND OF THE INVENTION

Before a living cell can reproduce, its DNA strands must unwind from their normal coiled configurations and assume a topology favorable for replication. To allow this unwinding the enzymes known as topoisomerases serve to introduce "swivels" in DNA strands. Without such a mechanism the DNA could not replicate, and hence the cell could not reproduce and proliferate. For detailed explanations of the topoisomerase function see A. Lehninger, Principles of Biochemistry, 813, Worth Publishers, New York (1982); F. Liu, "DNA Topoisomerases," CRC Critical Review in Biochemistry, 1-24, 15 (1983) and H Vosberg, "DNA Topoisomerases: Enzymes that Control DNA Conformation," Current Topics in Microbiology and Immunology, 19, Springer-Verlag, Berlin (1985). It has been recognized for some time that cell proliferation might be controlled by inhibition of topoisomerases and that such control might be particularly useful in halting the spread of tumors and related malignancies and ultimately destroying them. See E. Nelson, et al., Proc. Nat. Acad. Sci. U.S.A., 81, 1361 (1984).

On the basis of mechanism of action, topoisomerases have been categorized as Type I and Type II (often referred to as "topo I" and "topo II" respectively). The clinically useful antitumor agents adriamycin, mitoxantrone, etoposide and m-AMSA have been reported to work by inhibiting the function of Type II topoisomerase. Camptothecin, a natural product antitumor agent, has been found to inhibit the function of Type I topoisomerase. It is now believed that a compound which could effectively inhibit the functions of either or both Type I and Type II would be a potent antitumor agent.

SUMMARY OF THE INVENTION

One aspect of the present invention is the genus of the compounds of formula (I),

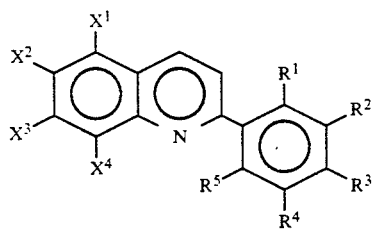

wherein:
$R^1$ is hydrogen, hydroxy or amino;
$R^2$ is hydrogen, hydroxy, methoxy or methoxymethoxy;
$R^3$ is hydrogen, hydroxy, amino, methoxy, methoxymethoxy, or, taken together with $R^2$, methylenedioxy (also known as 1,3 dioxolo);
$R^4$ is hydrogen, hydroxy, methoxy, methoxymethoxy, benzyl, di($C_{1-4}$)alkylaminomethyl or, taken together with $R^3$, methylenedioxy;
$R^5$ is hydrogen or hydroxy; provided that at least one of $R^1$ through $R^5$ is other than hydrogen; and i) $X^2$ is hydroxy or methoxy with $X^1$, $X^3$ and $X^4$ being hydrogen; or
ii) $X^1$ taken together with $X^2$, $X^2$ taken together with $X^3$ or $X^3$ taken together with $X^4$, is methylenedioxy, provided that each of the remaining respective $X^1$, $X^2$, $X^3$ and $X^4$ substituents are hydrogen.

Another aspect of the invention is a method of inhibiting topoisomerase Types I and II in mammalian cells comprising contacting these enzymes with a topoisomerase inhibiting amount of a compound of formula (I), and a method of treating a tumor in a mammal comprising administering to a mammal bearing a tumor, an antitumor amount of a compound of formula (I). A further aspect comprises pharmaceutical formulations containing a compound of formula (I) as an active ingredient. Novel chemical intermediates used in the synthesis, as taught herein, of the compounds of formula (I) are also within the scope of the present invention.

In particular, for the compounds of formula (I) di($C_{1-4}$)alkyl as used in di($C_{1-4}$)alkylaminomethyl means dimethyl, diethyl, dipropyl, diisopropyl and dibutyl (straight or branched).

DETAILED DESCRIPTION OF THE INVENTION

The preferred compounds of formula (I) are the compounds of formula (II)

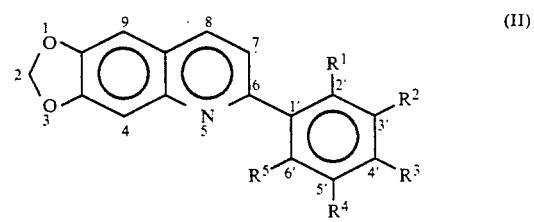

wherein $R^1$ through $R^5$ are the same as defined for formula (I). Specific compounds of formula (I) are:

| Compound Number | Compound Name |
| --- | --- |
| 1. | 6-(3,5-dimethoxy-4-hydroxy)phenyl-1,3-dioxolo[4,5-g]quinoline |
| 2. | 6-(4-hydroxy)phenyl-1,3-dioxolo[4,5-g]quinoline |
| 3a. | 6-[3-methoxy-4-(methoxymethoxy)phenyl]-1,3-dioxolo[4,5-g]quinoline |
| 3b. | 6-(4-hydroxy-3-methoxy)phenyl-1,3-dioxolo[4,5-g]quinoline |
| 4. | 6-(3,4,5-trimethoxy)phenyl-1,3-dioxolo[4,5-g]quinoline |
| 5. | 6-[3,4-(1,3-dioxolo)]phenyl-1,3-dioxolo[4,5-g]quinoline |
| 6. | 6-(3,4-dimethoxy)phenyl-1,3-dioxolo[4,5-g]quinoline |
| 7. | 6-(3,4-dihydroxy-5-methoxy)phenyl-1,3-dioxolo[4,5-g]quinoline |
| 8. | 6-(3,4-dimethoxy-5-hydroxy)phenyl-1,3-dioxolo[4,5-g]quinoline |
| 9. | 6-(3-benzyl-2,4-dihydroxy)phenyl-1,3-dioxolo[4,5-g]quinoline |
| 10. | 6-(2,4-dihydroxy)phenyl-1,3-dioxolo[4,5-g]quinoline |
| 11. | 6-[2,4-dihydroxy-3-(N,N-dimethylaminomethyl)]phenyl-1,3-dioxolo[4,5-g]quinoline |
| 12. | 6-[3,5-di(methoxymethoxy)]phenyl-1,3-dioxolo[4,5-g]quinoline |

As shown in Scheme (I):

SCHEME I

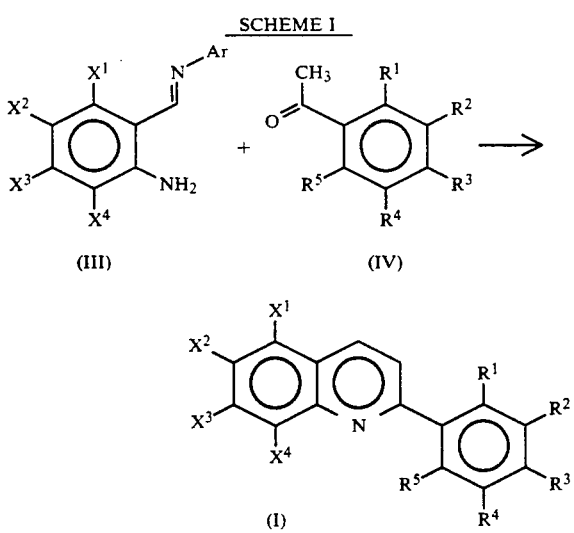

a compound of formula (III), wherein $X^1$ through $X^4$ are as defined for formula (I), and Ar is a $C_{6-12}$, one or two ring aromatic group (e.g., phenyl or 4-toluyl), may be reacted with a compound of formula (IV), wherein $R^1$ through $R^5$ are as defined for formula (I), to yield a corresponding compound of formula (I). This reaction may be conviently carried out in a suitable polar solvent system, for example, water, ($C_{1-4}$) alkanol, ($C_{2-4}$) alkylene diol or mixture thereof (e.g., water/ethanol) in the presence of a compatible strong mineral acid or alkali metal hydroxide base (e.g., sulfuric acid or sodium hydroxide) at a temperature in the range of from about 50° C. to about 150° C. See C. Cheng, "Friedländer Synthesis of Quinolines," Organic Reactions, 28, 37–201, John Wiley, New York (1982).

The compound of formula (I) prepared by this reaction scheme may be purified by conventional methods of the art, e.g., chromatography, distillation or crystallization.

Where $R^1$, $R^2$, $R^3$, $R^4$ or $R^5$ of a compound of formula (IV) or $X^2$ of a compound of formula (III) are base sensitive hydroxy functions, it is preferable to protect these functions by converting them into protected derivative functions, herein referred to collectively as "protected hydroxy functions " or "protected hydroxy," for example hydroxy protecting ether, e.g., alkoxyalkyl ethers or benzyl ethers, by methods known in the art, such as those methods taught in T. Green, Protective Groups in Organic Chemistry, Chap. 3, John Wiley, New York (1981). Protected hydroxy functions are stable to bases, compatible with basic catalysis conditions of the reaction of Scheme (I) and can conveniently be reconverted to the corresponding hydroxy functions by conventional techniques, such as those taught by T. Green, supra, e.g., treatment with acid, after completion of the reaction of Scheme (I).

Likewise, where $R^1$ and/or $R^3$ are the acid or base sensitive amino function, it is preferable to the protect the amino function by converting it into a protected amino derivative (herein, "protected amino"), e.g., an amide or a carbamate by methods known in the art, such as those methods taught in T. Green, supra, Chap. 7. Protected amino functions are selected to be compatible with acidic or basic catalysis conditions selected for the reaction of Scheme (I) and can conveniently be reconverted to the amino function by conventional techniques, such as those taught by T. Green, supra, e.g., hydrogenation using a palladium on carbon catalysis, after completion of the reaction of Scheme (I).

Compounds of formula (I) may be intraconverted to other compounds of formula (I). For example a compound of formula (I) bearing a methoxymethoxy function can be converted to a corresponding compound of formula (I) bearing an hydroxy function by treatment with a ($C_{1-4}$) alkanonic acid, e.g., refluxing in acetic acid. Further a compound of formula (I) where in $R^1$ and $R^3$ are hydroxy and $R^2$ is hydrogen can be reacted with (N,N-di($C_{1-4}$)alky)methyl ammonium halide in a suitable polar solvent such as a ($C_{1-4}$)alkanol in the presence of ($C_{1-4}$)alkyl trisubstitued amine, e.g., with (N,N-dimethyl)methyl ammonium iodide in ethanol and triethylamine at room temperature, to yield the corresponding compound of formula (I) wherein $R^1$ and $R^3$ are hydroxy and $R^2$ is N,N-di($C_{1-4}$)alkylmethylaminomethyl.

The compounds of formulas (III) and (IV) are either available commercially or may be prepared by methods of the art. For example, the compounds of formula (III) may be prepared by the methods taught by C. Cheng, supra, , and the compounds of formula (IV) may be prepared by the method taught by A. I. Vogel, Practical Organic Chemistry, 4th Ed., 773, Longmans, London (1978).

The intermediate compounds of formula (IA)

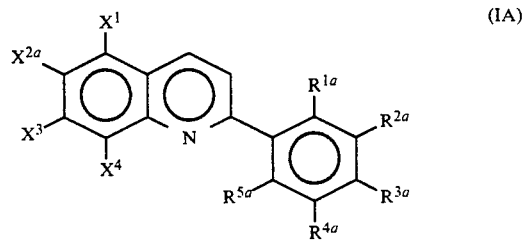

wherein:

$R^{1a}$ is hydrogen, protected hydroxy or protected amino;

$R^{2a}$ is hydrogen, protected hydroxy, methoxy or methoxymethoxy;

$R^{3a}$ is hydrogen, protected hydroxy, protected amino, methoxy, methoxymethoxy or, taken together with $R^2$, methylenedioxy;

$R^{4a}$ is hydrogen, protected hydroxy, methoxy, methoxymethoxy, benzyl, di($C_{1-4}$)alkylaminomethyl or, taken together with $R^3$, methylenedioxy;

$R^{5a}$ is hydrogen or hydroxy; provided that at least one of $R^1$ through $R^5$ is other than hydrogen; and i) $X^{2a}$ is protected hydroxy or methoxy with $X^1$, $X^3$ and $X^4$ being hydrogen; or ii) $X^1$ taken together with $X^{2a}$, $X^{2a}$ taken together with $X^3$ or $X^3$ taken together with $X^4$, is methylenedioxy, provided that each of the remaining respective $X^1$, $X^{2a}$, $X^3$ and $X^4$ substituents are hydrogen, are within the scope of the present invention. The preferred protected hydroxy functions are $-O-CH_2-O-CH_3$ and $-O-CH_2C_2H_5$, and the preferred protected amino functions are $-NHCOCH_3$ and $-NHCOOCH_3$.

Specific compounds of formula (IA) are:
6-(4-methoxymethoxy)phenyl-1,3-dioxolo[4,5-g]quinoline, 6-(3,4-dibenzyloxy-5-methoxy)phenyl-1,3-dioxolo[4,5-g]quinoline and
6-(3-benzyloxy-4,5-dimethoxy)phenyl-1,3-dioxolo[4,5-g]quinoline.
6-(2,4-dibenzyloxy)phenyl-1,3-dioxolo[4,5-g]quinoline The data from the Cleavable Complex Assay in Table A, below, shows the relative topoisomerase Types I and II inhibitory activity of the compounds of Formula (I). This assay performed according to the method described in Hsiang, Y. et al., *J. Biol. Chem.*, 260:14873-14878 (1985), correlates well with in vivo anti-tumor acivity of topoisomerase inhibitors in animal models of cancer, e.g., camptothecin and its analogs. See Hsiang et al., *Cancer Research*, 49:4385-4389 (1989) and Jaxel et al., *Cancer Research*, 49:1465-1469 (1989). In this assay compounds exhibiting no observable inhibitory activity at concentrations of greater than about 60 μg/mL (indicated by "−" in table A, below) are considered to be of no practical value as topoisomerase inhibitors. Those compounds which exhibit observable activity in the concentration range of from about 12 μg/mL to about 60 μg/mL ("+" in table A) are considered weakly active to moderately active, while those active in the range of from about 3 μg/mL to about 12 μg/mL ("++" in table A) are moderately active. Compounds active at concentrations less than 3 μg/mL ("+++" in table A) are considered to be strongly active topoisomerase inhibitors. Certain compounds of formula (I), e.g., compounds 1 and 10, inhibit both Type I and Type II topoisomerase.

TABLE A

Topoisomerase Inhibitory Activity of Compounds of Formula (I) in the Cleavable Complex Assay

| Compound Number | Topo I | Topo II |
| --- | --- | --- |
| 1 | +++ | + |
| 2 | + | − |
| 3a | + | − |
| 3b | + | − |
| 4 | +++ | − |
| 5 | + | − |
| 6 | ++ | − |
| 7 | − | + |
| 8 | − | + |
| 9 | − | ++ |
| 10 | +++ | +++ |
| 11 | − | + |
| 12 | + | − |

"−" Indicates no activity of practical value.
"+" Indicates positive activity, and the number of "+" signs indicates relative activity (see description of this assay, above).

The compounds of formula (I) are active against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, etc. The compounds of formula (I) may also be used in combination with other therapeutic agents, for example, other antitumor agents. Herein the terms "tumor", "cancer" and "cancerous growths" are used synonymously.

The amount of compound of formula (I) required to be effective as an antitumor agent will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective antitumor dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, the preferable dose range would be about 75 to about 7500 mg per day, and a typical dose would be about 800 mg per day. If discrete multiple doses are indicated, treatment might typically be 200 mg of a compound of formula (I) given 4 times per day.

Formulations of the present invention, for medical use, comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier therefor.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. Such unit dosage form contains, e.g., 10 to 1000 mg, conveniently 15 to 500 mg, most conveniently from 20 to 200 mg of active ingredient. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal or vaginal administration may be presented as a suppository with a conventional carrier, e.g., cocoa butter or Witepsol S55 (trademark of Dynamite Nobel Chemical, Germany, for a suppository base).

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter. Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, preservatives (including antioxidants) and the like.

EXAMPLES

The following examples illustrate aspects of this invention but should not be construed as limitations. The symbols and conventions used in these examples are consistent with those used in the contemporary chemical literature, for example, the Journal of the American Chemical Society.

EXAMPLE 1

6-(3,5-dimethoxy-4-hydroxy)phenyl-1,3-dioxolo[4,5-g]quinoline (Compound 1)

To 3,5-dimethoxy-4-hydroxy acetophenone (196 mg, 1 mmol) is added 6[[(4-methylphenyl)imino]methyl]-1,3-benzodioxol-5-amine (255 mg, 1 mmol) in ethanol (4 mL) and 2N sodium hydroxide (1 mL). The reaction mixture is heated at reflux (about 100° C.) for 16 hrs. Upon cooling the reaction product is dissolved in methylene chloride (200 mL) and extracted with a saturated sodium chloride solution (200 mL). The organic layer is dried with a rotatory evaporator. The resulting residue is chromatographed on silica gel with 2:3 ethyl acetate/hexanes to yield 6-(3,5-dimethoxy-4-hydroxy)phenyl-1,3-dioxolo[4,5-g]quinoline (54 mg, 16.6% of theory).

$^1$H-300 NMR (CDCl$_3$): δ 4.06 (s, 6H); 5.73 (s, 1H); 6.15 (s, 2H); 7.09 (s, 1H); 7.42 (s, 2H); 7.48 (s, 1H); 7.69 (d, J=8.55 Hz, 1H); 8.03 (d, J=8.55 Hz, 1H).

| Elemental analysis: (for C$_{18}$H$_{15}$NO$_5$) | | | |
|---|---|---|---|
| | % C | % H | % N |
| Found: | 66.51 | 4.66 | 4.33 |
| Calculated: | 66.46 | 4.65 | 4.31 |

EXAMPLE 2

6-(4-hydroxy)phenyl-1,3-dioxolo[4,5-g]quinoline (Compound 2)

(A.) 4-(Methoxymethyleneoxy)acetophenone (3.84 g, 21.3 mmol) is reacted with 6[[(4-methylphenyl)imino]methyl]-1,3-benzodioxol-5-amine (5.42 g, 21.3 mmol) in ethanol (4 mL) and 2N sodium hydroxide (1 mL), and the product recovered and isolated in a similar manner to Example 1 to yield 6-(4-methoxymethoxy)phenyl-1,3-dioxolo[4,5-g]quinoline (3.24 g, 49.2% theory), $^1$H-300 NMR (CDCl$_3$): δ 3.55 (s, 3H); 5.28 (s, 2H); 6.13 (s, 2H); 7.07 (s, 1H); 7.20 (d, J=9.0 Hz, 2H); 7.46 (s, 1H); 7.70 (d, J=8.55 Hz, 1H); 8.01 (d, J=8.30 Hz, 1H); 8.09 (d, J=8.79 Hz, 2H).

(B.) The compound prepared in part (A) above (314 mg, 1.01 mmol) is heated in glacial acetic acid (4 mL) at reflux (about 118° C.) under nitrogen for approximately 24 hrs. The reaction product is concentrated by rotatory evaporation to remove the acetic acid, and the residue is dissolved in 100 mL of methylene chloride and then washed with sodium bicarbonate solution. The organic layer is dried with magnesium sulfate, filtered and concentrated on a rotary evaporator. The residue is dissolved in minimal hot methylene chloride and hexane is slowly added to induce precipitation of the product, 6-(4-hydroxy)phenyl-1,3-dioxolo[4,5-g]quinoline, (103 mg, 38.4% theory). $^1$H-300 NMR (CDCl$_3$): δ 5.80 (s, 2H); 6.64 (d, J=8.80 Hz, 2H); 6.75 (s, 1H); 7.10 (s, 1H); 7.35 (d, J=8.54 Hz, 1H); 7.66 (d, J=8.79 Hz, 2H); 7.69 (d, J=8.55 Hz, 1H); 8.83 (s, 1H).

Exact Mass High Resolution Mass: (for C$_{16}$H$_{11}$No$_3$); Calculated: 266.0817. Found: 266.0833.

EXAMPLE 3

6-[3-methoxy-4-(methoxymethoxy)]phenyl-1,3dioxolo[4,5-g]quinoline (Compound 3a) and
6-(4-hydroxy-3-methoxy)phenyl-1,3-dioxolo[4,5-g]quinoline (Compound 3b)

(A.) 3-Methoxy-4-methoxymethoxyacetophenone (1.16 g, 5.51 mol) is reacted with 6[[(4-methylphenyl)imino]methyl]-1,3-benzodioxol-5-amine (1.40 g, 5.51 mmol) in ethanol (4 mL) and 2N sodium hydroxide (1 mL), and the product recovered and isolated in a similar manner to Example 1 to yield 6-[3-methoxy-4-(methoxymethoxy)phenyl]-1,3 dioxolo [4,5-g]quinoline (1.28 g, 67.7% theory).

$^1$H-300 NMR (CDCl$_3$): δ 3.58 (s, 3H); 4.07 (s, 3H); 5.34 (s, 2H); 6.14 (s, 2H); 7.08 (s, 1H); 7.29 (d, J=8.3 Hz, 1H); 7.48 (s, 1H); 7.59 (d of d, J=8.3, 1.9 Hz, 1H); 8.55 (d, J=8.55 Hz, 1H); 7.85 (m, 1H); 8.01 (d, J=8.54 Hz, 1H)

| Elemental analysis: (for C$_{19}$H$_{17}$NO$_5$) | | | |
|---|---|---|---|
| | % C | % H | % N |
| Found: | 67.35 | 5.08 | 4.14 |
| Calculated: | 67.25 | 5.05 | 4.13 |

(B.) The compound prepared in part (A), above, (250 mg, 0.74 mmol) is heated at about 100° C. in refluxing tetrahydrofuran 2.5 mL, 95% ethanol (2.5 mL) and 20% aqueous HCl (2.5 mL) for 16 hrs. The reaction product is then washed with a saturated sodium bicarbonate solution, dried with magnesium sulfate, filtered and concentrated on a rotary evaporator. The resulting concentrate is chromatographed on silica gel with 1:1 ethyl acetate/hexanes to yield 6-(4-hydroxy-3-methoxy)phenyl-1,3-dioxolo[4,5-g]quinoline (151 mg, 69.6% theory).

$^1$H-300 NMR (CDCl$_3$): δ 4.04 (s, 3H); 6.11 (s, 2H); 6.57 (s, 1H); 7.01 (d, J=8.3 Hz, 1H); 7.05 (s, 1H); 7.44 (s, 1H); 7.54 (d of d, J=8.3 Hz, 1.95 Hz, 1H); 7.67 (d, J=8.55 Hz, 1H); 7.79 (m, 1H); 7.98 (d, J=8.55 Hz, 1H)

| Elemental analysis: (for C$_{17}$H$_{13}$NO$_4$) | | | |
|---|---|---|---|
| | % C | % H | % N |
| Found: | 68.69 | 4.68 | 4.72 |
| Calculated: | 69.15 | 4.44 | 4.74 |

EXAMPLE 4

6-(3,4,5-trimethoxy)phenyl-1,3-dioxolo[4,5-g]quinoline (Compound 4)

3,4,5-Trimethoxyacetophenone (210 mg, 1 mmol) is reacted with 6[[(4-methylphenyl)imino]methyl]-1,3-benzodioxol-5-amine (255 mg, 1 mmol) in ethanol (4 mL) and 2N sodium hydroxide (1 mL), and the product recovered and isolated in a similar manner to Example 1 to yield 6-(3,4,5-trimethoxy)phenyl-1,3-dioxolo[4,5-g]quinoline (223 mg, 65.7% theory).

$^1$H-300 NMR (CDCl$_3$): δ 3.95 (s, 3H); 4.04 (s, 6H); 6.16 (s, 2H); 7.11 (s, 1H); 7.38 (s, 1H); 7.52 (s, 2H); 8.03 (d, J=8.5 Hz, 1H); 8.06 (d, J=8.3 Hz, 1H)

| Elemental analysis: (for C$_{19}$H$_{17}$NO$_5$) | | | |
|---|---|---|---|
| | % C | % H | % N |
| Found: | 67.24 | 5.06 | 4.14 |
| Calculated: | 67.25 | 5.05 | 4.13 |

EXAMPLE 5

6-[3,4-(1,3-dioxolo)]phenyl-1,3-dioxolo[4,5-g]quinoline (Compound 5)

3,4-Methlenedioxyacetophenone (187 g, 1.14 mmol) is reacted with 6[[(4-methylphenyl)imino]methyl]-1,3-benzodioxol-5-amine (1.04, 264 mmol) in ethanol (4 mL) and 2N sodium hydroxide (1 mL), and the product recovered and isolated in a similar manner to Example 1 to yield 6-[3,4-(1,3-dioxolo)]phenyl-1,3-dioxolo[4,5-g]quinoline (175 mg, 57.4% theory).

$^1$H-300 NMR (CDCl$_3$): δ 6.06 (s, 2H); 6.14 (s, 2H); 6.69 (d, 1H); 7.08 (s, 1H); 7.45 (s, 1H); 8.0 to 7.62 (m, 3H); 8.01 (d, J=8.54 Hz, 1H).

High resolution Exact Mass: (for C$_{17}$H$_{11}$NO$_4$); Calc=294.0766. Found=294.0782.

EXAMPLE 6

6-(3,4-dimethoxy)phenyl-1,3-dioxolo[4,5-g]quinoline (Compound 6)

3,4-Dimethoxyacetophenone (180 mg, 1 mmol) is reacted with 6[[(4-methylphenyl)imino]methyl]-1,3-benzodioxol-5amine (255 mg, 1 mmol) in ethanol (4 mL) and 2N sodium hydroxide (1 mL), and the product recovered and isolated in a similar manner to Example 1 to yield 6-(3,4-dimethoxy)phenyl-1,3-dioxolo[4,5-g]quinoline (106 mg, 34.3% theory).

$^1$H-300 NMR (CDCl$_3$): δ 3.99 (s, 3H); 4.07 (s, 3H); 6.14 (s, 2H); 7.02 (d, J=8.3 Hz, 1H); 7.09 (s, 1H); 7.45 (s, 1H); 7.64 (d, J=8.3 Hz, 1H); 7.72 (d, J=8.79 Hz, 1H); 7.83 (s, 1H); 8.02 (d, J=8.3, 1H)

| Elemental analysis: (for C$_{18}$H$_{15}$NO$_4$) | | | |
|---|---|---|---|
| | % C | % H | % N |
| Found: | 69.23 | 4.90 | 4.62 |
| Calculated: | 69.89 | 4.89 | 4.53 |

EXAMPLE 7

6-(3,4-dihydroxy-5-methoxy)phenyl-1,3-dioxolo[4,5-g]quinoline (Compound 7)

(A.) 3,4-Dibenzyloxy-5-methoxyacetophenone (5.07 g, 14 mmol) is reacted with 6[[(4-methylphenyl)imino]methyl]-1,3-benzodioxol-5-amine (3.56 g, 14 mmol) in ethanol (56 mL) and 2N sodium hydroxide (14 mL), and the product recovered and isolated in a similar manner to Example 1 to yield 6-(3,4-dibenzyloxy-5-methoxy)phenyl-1,3-dioxolo[4,5-g]quinoline (1.18 g, 17.1% theory).

$^1$H-300 NMR (CDCl$_3$): δ 4.01 (s, 3H); 5.14 (s, 2H); 5.26 (s, 2H); 6.15 (s, 2H); 7.10 (s, 1H); 7.53 to 7.32 (m, 13H); 7.66 (d, J=8.54 Hz, 1H); 8.03 (d, J=8.3 Hz, 1H)

(B.) The compound prepared in part (A) above (872 mg, 1.77 mmol), ethyl acetate, 40 mL, dry tetrahydrofuran, 10 mL, and 10% palladium on carbon (350 mg) are stirred under hydrogen at 1 atmosphere pressure and ambient temperture (about 25° C.) for about 16 hrs. The reaction mixture is filtered through a pad of diatomaous earth filter aid then concentrated with a rotatory evaporator. The concentrate is taken up in a minimum of dichloromethane and precipitated with excess hexanes. The resulting precipitate is collected and dried in vacuo for about 16 hrs. to yield 6-(3,4-dihydroxy-5-methoxy)phenyl-1,3-dioxolo[4,5-g]quinoline (261 mg, 47.4% theory).

$^1$H-300 NMR (CDCl$_3$): δ 4.05 (s, 3H); 5.7 (s, 1H); 6.14 (s, 2H); 7.09 (s, 1H); 7.31 (s, 1H); 7.33 (s, 1H); 7.43 (s, 1H); 7.47 (s, 1H); 7.67 (d, J=8.54 Hz, 1H); 8.02 (d, J=8.55 Hz, 1H)

EXAMPLE 8

6-(3,4-dimethoxy-5-hydroxy)phenyl-1,3-dioxolo[4,5-g]quinoline (Compound 8)

(A.) 3-Benzyloxy-4,5-dimethoxyacetophenone (1.64 g, 5.71 mmol) is reacted with 6[[(4-methylphenyl)imino]methyl]-1,3-benzodioxol-5-amine (1.46 g, 5.71 mmol) in ethanol (4 mL) and 2N sodium hydroxide (1 mL), and the product recovered and isolated in a similar manner to Example 1 to yield 6-(3-benzyloxy-4,5-dimethoxy)phenyl-1,3-dioxolo[4,5-g]quinoline (427 mg, 18% theory).

$^1$H-300 NMR (CDCl$_3$): δ 3.97 (s, 3H); 4.04 (s, 3H); 5.3 (s, 2H); 6.15 (s, 2H); 7.10 (s, 1H); 7.56 to 7.29 (m, 8H); 7.64 (d, 1H); 8.02 (d, 1H)

(B.) The compound prepared in part (A) (390 mg, 0.094 mmol), is catalytically hydrogenated, and the product recovered and isolated in a similar manner to Example 7, part (B), to yield 2-(3,4-dimethoxy-5- hydroxyphenyl)-6,7-(1,3-dioxolo)quinoline (201 mg, 65.9% theory).

$^1$H-300 NMR (CDCl$_3$): δ 3.99 (s, 3H); 4.05 (s, 3H); 5.90 (s, 1H); 6.15 (s, 2H); 7.10 (s, 1H); 7.31 (s, 1H); 7.41 (d, J=1.95 Hz, 1H); 7.48 (s, 1H); 7.67 (d, J=8.5 Hz, 1H); 8.01 (d, J=8.3 Hz, 1H)

High Resolution Exact Mass: (for C$_{18}$H$_{15}$NO$_5$); Calc=326.1028. Found=326.1014.

EXAMPLE 9

6-(3-benzyl-2,4-dihydroxy)phenyl-1,3-dioxolo[4,5-g]quinoline (Compound 9)

(A.) To sodium hydride, 0.88 g (60% in mineral oil, 0.022 mol) and 5 mL dry THF under N$_2$ is added dropwise 1.52 g (0.01 mol) 2,4-dihydroxyacetophenone in 5 mL THF. After stirring for 30 min., a solution of 2.6 mL (0.022 mol) of benzyl bromide in 5 mL THF is reacted with dropwise. The reaction is then heated to reflux (about 66°) for 16 hrs., allowed to cool, filtered and diluted with 40 mL EtOAc then washed with 1N HCl (2×20 mL), H$_2$O (20 ml), 2N NaOH (3×20 ml), H$_2$O (2×20 ml) and brine (20 mL). The organic layer is dried (MgSO$_4$), then concentrated in vacuo and is dried to give 3.31 g of amber syrup. This syrup is flash chromatographed (55 mm×175 mm) using hexane as solvent to recover 2,4-dibenzyloxyacetophenone as a yellow solid and 2,4-dibenzyloxy-3-benzylacetophenone as an orange syrup.

2,4-dibenzyloxyacetophenone: $^1$H-NMR: (CDCl$_3$): δ 2.56(s,3H), 5.09(s,2H), 5.11 (s,2H), 6.60(d, 1H,J=1.0 Hz), 6.61 (dd, 1H,J=10 Hz,J=1.0 Hz), 7.28-7.46(m, 10H), 7.84(d, 1H, J=1-Hz) MS(El): m/e=332 (C$_{22}$H$_{20}$O$_3$)

2,4-dibenzyloxy-3-benzylacetophenone: $^1$H-NMR: (CHCl$_3$): δ 2.60(s,3H), 4.11(s,2H), 4.78(s,2H), 5.1(s,2H), 6.81(d,1H,J=8.7 Hz), 7.18-7.39(m,15H), 7.63(d,1H,J=8.7 Hz) MS(El): m/e=422 (C$_{29}$H$_{26}$O$_3$)

(B) To a 60:40 mixture of 2,4-dibenzyloxyacetophenone and dibenzyloxy-3-benzyl 2,4-acetophenone (3.27 g) prepared in Example 9 (A) are added 2.49 g 6[[(4-methylphenyl)imino]methyl]-1,3-benzodioxol-5-amine, 10 mL 2N NaOH and 40 mL EtOH and the mixture is refluxed (about 100° C.) for 2 days. The reaction is cooled and filtered to remove insolubles, and the filtrate is concentrated in vacuo. The residue is redissolved in 80 mL EtOAc and washed successively with H$_2$O(3×20 ml) and brine (20 ml). The organic material is dried over MgSO$_4$, concentrated in vacuo and the resulting oil is flash chromatographed (175 mm×49 mm) using a gradient solvent system of 10% EtOAc/hexane to recover 1.75 g of a yellow solid as a 60:40 mixture of 6-(2,4-dibenzyloxy)phenyl-1,3-dioxolo[4,5-g]quinoline and 6-(3-benzyl-2,4-dibenzyloxy)phenyl-1,3-dioxolo[4,5-g]quinoline according to $^1$H-NMR.

(C) The compound mixture prepared in part (B), above, (1.75 g), ethanol (100 mL), tetrahydrofuran (50 mL) and a 10% palladium on carbon catalyst (1.0 g) are shaken in a hydrogen atmosphere (about 50 psi) for about 11 hrs. The reaction product is diluted with ethyl acetate and filtered to remove the Pd/C catalyst. The filtrate is concentrated by rotatory evaporation to give a residue which is recrystallized from ethanol to yield 6-(3-benzyl-2,4-dihydroxy)phenyl-1,3-dioxolo[4,5 g]quinoline (123.4 mg, 17.4% theory) as an amber solid.

$^1$H-300 NMR (DMSO-d$_6$)): δ 3.95 (s,2H), 6.20 (s,2H); 6.49 (d, J=8.79 Hz, 1H); 7.05-7.29 (m, 5H), 7.35 (s, 1H); 7.43 (s, 1H); 7.82 (d, J=9.03 Hz, 1H, ArH); 7.99 (d,J=9.03 Hz, 1H); 8.24 (d, J=9.03 Hz, 1H); 9.88 (s, 1H)

| Elemental analysis: (for C$_{23}$H$_{17}$NO$_4$) | | | |
|---|---|---|---|
| | % C | % H | % N |
| Found: | 73.40 | 4.72 | 3.72 |
| Calculated: | 74.46 | 4.62 | 3.77 |

EXAMPLE 10

6-(2,4-dihydroxy)phenyl-1,3-dioxolo[4,5-g]quinoline (Compound 10)

(A) 2,4-Dibenxloxyacetophenone (320 mg, 0.96 mmol) is reacted with 6[[(4-methylphenyl)imino]methyl]-1,3-benzodioxol-5-amine (249 mg, 0.98 mmol) in ethanol (4 mL) and 2N sodium hydroxide (1 mL), and the product recovered and isolated in a similar manner to Example 1 to yield 6-(2,4-dibenzyloxy)phenyl-1,3-dioxolo[4,5-g]quinoline (80.1 mg, 18% theory).

m.p. 143°-144° C.

MS(El):m/e=461 (C$_{30}$H$_{23}$NO$_4$).

(B) The compound prepared in part (A) above, 6-(2,4-dibenzyloxy)phenyl-1,3-dioxolo[4,5-g]quinoline (1.0 g, 2.2 mmol), in ethyl acetate (60 mL) with 10% palladium on carbon (0.5 g) is treated with hydrogen at 50 psi for about two and a half days, and the product recrystallized from ethanol to yield 6-(2,4-dihydroxy)-phenyl-1,3-dioxolo[4,5-g]quinoline (357.1 mg, 58.6% theory).

$^1$H-300 NMR (CDCl$_3$): δ 6.20 (s, 2H); 6.30 (d, 1H, J=2.44 Hz); 6.37 (dd, 1H, J=8.79 Hz, J=2.44 Hz); 7.34 (s, 1H), 7.37 (s, 1H), 7.89 (d, 1H, J=8.79 Hz); 7.96 (d, 1H, J=9.03 Hz); 8.22 (d, 1H, J=8.79 Hz); 9.85 (s, 1H).

| Elemental analysis: (for C$_{16}$H$_{11}$NO$_4$) | | | |
|---|---|---|---|
| | % C | % H | % N |
| Found: | 68.22 | 3.96 | 4.96 |
| Calculated: | 68.32 | 3.94 | 4.98 |

EXAMPLE 11

6-[2,4 dihydroxy-3-(N,N-dimethylaminomethyl)]phenyl-1,3-dioxolo[4,5-g]quinoline (Compound 11)

Compound 10, i.e., 6-(2,4-dihydroxy)phenyl-1,3-dioxolo[4,5-g]quinoline (50 mg, 0.18 mmol), triethylamine (0.025 mL, 0.18 mmol) and EtOH (2.0 mL) is reacted with 33.3 mg (N,N-dimethyl)methyl ammonium iodide and the mixture stirred at ambient temperature (about 25° C.) for 24 hrs. The reaction mixture is concentrated in vacuo and the resulting yellow solid is dry charged onto a flash column (20 mm×175 mm) and eluted with 10% MeOH/CHCl$_3$ to recover 50.2 mg of 6-[2,4-dihydroxy-3-(N,N-dimethylaminomethyl)]phenyl-1,3-dioxolo[4,5-g]quinoline as a yellow solid.

mp= >250

$^1$H-NMR: (CDCl$_3$) 2.68(6,s), 4.15(s,2H), 6.23(s,2H), 6.51 (d, J=8.8 Hz, 1H), 7.39(s,1H), 7.4(s,1H), 8.03(d, J=9.0 Hz, 1H), 8.05(d,J=9.0 Hz, 1H), 8.30(d, J=8.8 Hz, 1H), 8.31(s,1H)

High Resolution Exact Mass: (for C$_{19}$H$_{18}$N$_2$O$_4$); Calc.=339.1353. Found=339.1345.

EXAMPLE 12

6-[3,5-di(methoxymethoxy)phenyl]-1,3-dioxolo[4,5-g]quinoline (Compound 12)

3,5-Di(methoxymethoxy)acetophenone (480 mg, 2 mmol) is reacted with 6[[(4-methylphenyl)imino]methyl]-1,3-benzodioxol-5-amine (510 mg, 2 mmol) in ethanol (4 mL) and 2N sodium hydroxide (1 mL), and the product recovered and isolated in a similar manner to Example 1 to yield 6-[3,5-di(methoxymethoxy)phenyl]-1,3-dioxolo[4,5-g]quinoline (472 mg, 64.5% theory).

| Elemental analysis: (for $C_{20}H_{19}NO_6$) | | | |
|---|---|---|---|
| | % C | % H | % N |
| Found: | 64.93 | 5.19 | 3.79 |
| Calculated: | 65.03 | 5.18 | 3.79 |

EXAMPLE 13

2-(3,4-dihydroxy-5-methoxy)phenyl-6-hydroxyquinoline

This compound is prepared by the same procedure of Example 7 except that an equivalent amount of N-[[2-amino-5-[(4-methoxyphenyl)methoxy]phenyl]-4-methyl benzene amine is used in place of 6[[(4-methylphenyl)imino]methyl]-1,3-benzodioxol-5-amine. The protecting (4-methyoxyphenyl)methylene group can be removed by catalytic hdrogenation as taught by Green, supra, to yield 2-(3,4-dihydroxy-5-methoxy)phenyl-6-hydroxyquinoline

EXAMPLES 14–16

In a manner similar to the above Examples, and as described in the specification above, the following compounds of formula (I) can be prepared:

| | Formula (I) | | | | | | | | |
|---|---|---|---|---|---|---|---|---|---|
| Example | $X^1$ | $X^2$ | $X^3$ | $X^4$ | $R^1$ | $R^2$ | $R^3$ | $R^4$ | $R^5$ |
| 14 | —OCH$_2$O— | | H | H | H | OH | H | H | H |
| 15 | H | H | —OCH$_2$O— | | OH | H | H | H | OH |
| 16 | H | OCH$_3$ | H | H | H | H | NH$_2$ | H | H |

EXAMPLE 17

Pharmaceutical formulations

| (A) Transdermal System | |
|---|---|
| Ingredients | Amount |
| Active compound | 600.0 mg |
| Silicone fluid | 450.0 mg |
| Colloidal silicone dioxide | 25.0 mg |

The silicone fluid and active compound are mixed together and the colloidal silicone dioxide is reacted with to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

| (B) Oral Tablet | |
|---|---|
| Ingredients | Amount |
| Active compound | 200.0 mg |
| Starch | 20.0 mg |
| Magnesium Stearate | 1.0 mg |

The active compound and the starch are granulated with water and dried. Magnesium stearate is added to the dried granules and the mixture is thoroughly blended. The blended mixture is compressed into a tablet.

| (C) Suppository | |
|---|---|
| Ingredients | Amount |
| Active compound | 150.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

| (D) Injection | |
|---|---|
| Ingredients | Amount |
| Active Compound | 20.0 mg |
| Buffering Agents | q.s. |
| Propylene glycol | 0.4 |
| Water for injection | 0.6 mL |

The active compound and buffering agents are dissolved in the propylene glycol at about 50° C. The water for injection is then added with stirring and the resulting solution is filtered, filled into an ampule, sealed and sterilized by autoclaving.

| (E) Capsule | |
|---|---|
| Ingredients | Amount |
| Active Compound | 200.0 mg |
| Lactose | 450.0 mg |
| Magnesium stearate | 5.0 mg |

The finely ground active compound is mixed with the lactose and stearate and packed into a gelatin capsule.

We claim:

1. A compound of formula (I)

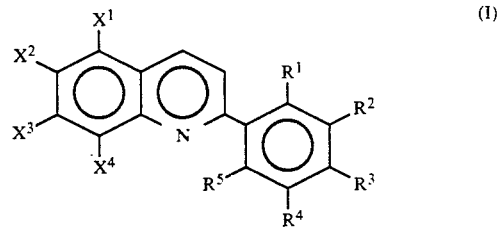

wherein:

$R^1$ is hydrogen or hydroxy;

$R^2$ is hydrogen, hydroxy, methoxy or methoxymethoxy;

$R^3$ is hydrogen, hydroxy, amino, methoxy, methoxymethoxy or, taken together with $R^2$, methylenedioxy;

R⁴ is hydrogen, hydroxy, methoxy, methoxymethoxy, benzyl, di(C₁₋₄)alkylaminomethyl or, taken together with R³, methylenedioxy;

R⁵ is hydrogen or hydroxy; provided that at least one of R¹ through R⁵ is other than hydrogen; and X¹ taken together with X², X² taken together with X³ or X³ taken together with X⁴, is methylenedioxy, provided that each of the remaining respective X¹, X², X³ and X⁴ substituents are hydrogen.

2. A compound of claim 1 which is a compound of formula (II).

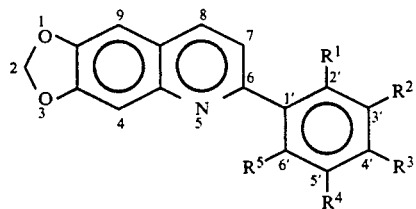

(II)

3. A compound of claim 1 wherein R¹ is hydrogen and R², R³, R⁴ and R⁵ are hydrogen or hydroxy.

4. A compound of claim 1 wherein R¹ and R⁵ are each hydrogen, R² and R⁴ are each methoxy, and R³ is hydroxy.

5. A compound of claim 1 wherein R¹ and R³ are each hydroxy, and R², R⁴ and R⁵ are each hydrogen.

6. The compound of claim 1 which is:
6-(3,5-dimethoxy-4-hydroxy)phenyl-1,3-dioxolo[4,5-g]quinoline,
6-(4-hydroxy)phenyl-1,3-dioxolo[4,5-g]quinoline,
6-[3-methoxy-4-(methoxymethoxy)phenyl]-1,3-dioxolo[4,5-g]quinoline,
6-(4-hydroxy-3-methoxy)phenyl-1,3-dioxolo[4,5-g]quinoline,
6-(3,4,5-trimethoxy)phenyl-1,3-dioxolo[4,5-g]quinoline,
6-[3,4-(1,3-dioxolo)]phenyl-1,3-dioxolo[4,5-g]quinoline,
6-(3,4-dimethoxy)phenyl-1,3-dioxolo[4,5-g]quinoline,
6-(3,4-dihydroxy-5-methoxy)phenyl-1,3-dioxolo[4,5-g]quinoline,
6-(3,4-dimethoxy-5-hydroxy)phenyl-1,3-dioxolo[4,5-g]quinoline,
6-(3-benzyl-2,4-dihydroxy)phenyl-1,3-dioxolo[4,5-g]quinoline,
6-(2,4-dihydroxy)phenyl-1,3-dioxolo[4,5-g]quinoline or
6-[2,4-dihydroxy-3-(N,N-dimethylaminomethyl)]-phenyl-1,3-dioxolo[4,5-g]quinoline.

7. A pharmaceutical composition comprising a compound of formula (I)

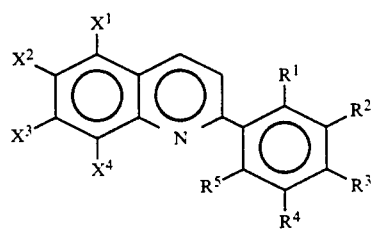

(I)

wherein:
R¹ is hydrogen or hydroxy;

R² is hydrogen, hydroxy, methoxy or methoxymethoxy;

R³ is hydrogen, hydroxy, amino, methoxy, methoxymethoxy or, taken together with R², methylenedioxy;

R⁴ is hydrogen, hydroxy, methoxy, methoxymethoxy, benzyl, di(C₁₋₄)alkylaminomethyl or, taken together with R³, methylenedioxy;

R⁵ is hydrogen or hydroxy; provided that at least one of R¹ through R⁵ is other than hydrogen; and X¹ taken together with X², X² taken together with X³ or X³ taken together with X⁴, is methylenedioxy, provided that each of the remaining respective X¹, X², X³ and X⁴ substituents are hydrogen and a pharmaceutically acceptable carrier thereof.

8. A method of inhibiting a topoisomerase enzyme comprising contacting said enzyme with an effective inhibitory amount of a compound of formula (I)

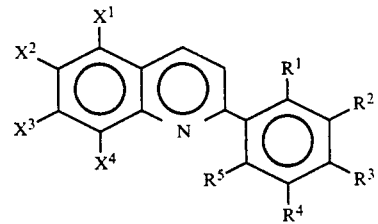

(I)

wherein:
R¹ is hydrogen or hydroxy;

R² is hydrogen, hydroxy, methoxy or methoxymethoxy;

R³ is hydrogen, hydroxy, amino, methoxy, methoxymethoxy or, taken together with R², methylenedioxy;

R⁴ is hydrogen, hydroxy, methoxy, methoxymethoxy, benzyl, di(C₁₋₄)alkylaminomethyl or, taken together with R³, methylenedioxy;

R⁵ is hydrogen or hydroxy; provided that at least one of R¹ through R⁵ is other than hydrogen; and X¹ taken together with X², X² taken together with X³ or X³ taken together with X⁴, is methylenedioxy, provided that each of the remaining respective X¹, X², X³ and X⁴ substituents are hydrogen.

9. A method of claim 8 wherein a compound of formula (I) is a compound of formula (II).

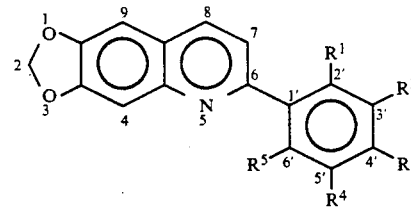

(II)

10. A method of claim 8 wherein the compound of formula (I) is
6-(3,5-dimethoxy-4-hydroxy)phenyl-1,3-dioxolo[4,5-g]quinoline,
6-(4-hydroxy)phenyl-1,3-dioxolo[4,5-g]quinoline,
6-[3-methoxy-4-(methoxymethoxy)phenyl]-1,3-dioxolo[4,5-g]quinoline,
6-(4-hydroxy-3-methoxy)phenyl-1,3-dioxolo[4,5-g]quinoline, 6-(3,4,5-trimethoxy)phenyl-1,3-dioxolo[4,5-g]quinoline,
6-[3,4-(1,3-dioxolo)]phenyl-1,3-dioxolo[4,5-g]quinoline,
6-(3,4-dimethoxy)phenyl-1,3-dioxolo[4,5-g]quinoline,
6-(3,4-dihydroxy-5-methoxy)phenyl-1,3-dioxolo[4,5-g]quinoline,
6-(3,4-dimethoxy-5-hydroxy)phenyl-1,3-dioxolo[4,5-g]quinoline,
6-(3-benzyl-2,4-dihydroxy)phenyl-1,3-dioxolo[4,5-g]quinoline,
6-(2,4-dihydroxy)phenyl-1,3-dioxolo[4,5-g]quinoline or
6-[2,4-dihydroxy-3-(N,N-dimethylaminomethyl)]-phenyl-1,3-dioxolo[4,5-g]quinoline.

11. A method of treating a tumor in a mammal comprising administering to said mammal, an effective antitumor amount of a compound of formula (I)

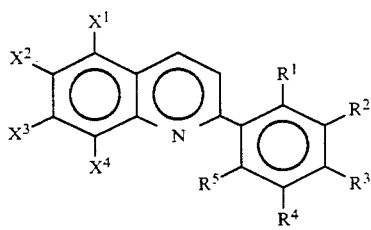

wherein:
$R^1$ is hydrogen or hydroxy;
$R^2$ is hydrogen, hydroxy, methoxy or methoxymethoxy;
$R^3$ is hydrogen, hydroxy, amino, methoxy, methoxymethoxy or, taken together with $R^2$, methylenedioxy;
$R^4$ is hydrogen, hydroxy, methoxy, methoxymethoxy, benzyl, di($C_{1-4}$)alkylaminomethyl or, taken together with $R^3$, methylenedioxy;
$R^5$ is hydrogen or hydroxy; provided that at least one of $R^1$ through $R^5$ is other than hydrogen; and
$X^1$ taken together with $X^2$, $X^2$ taken together with $X^3$ or $X^3$ taken together with $X^4$, is methylenedioxy, provided that each of the remaining respective $X^1$, $X^2$, $X^3$ and $X^4$ substituents are hydrogen.

12. A method of claim 11 wherein said mammal is a human.

13. A method of claim 11 wherein the compound of formula (I) is
6-(3,5-dimethoxy-4-hydroxy)phenyl-1,3-dioxolo[4,5-g]quinoline,
6-(4-hydroxy)phenyl-1,3-dioxolo[4,5-g]quinoline,
6-[3-methoxy-4-(methoxymethoxy)phenyl[-1,3-dioxolo[4,5-g]quinoline,
6-(4-hydroxy-3-methoxy)phenyl-1,3-dioxolo[4,5-g]quinoline,
6-(3,4,5-trimethoxy)phenyl-1,3-dioxolo[4,5-g]quinoline,
6-[3,4-(1,3-dioxolo)]phenyl-1,3-dioxolo[4,5-g]quinoline.
6-(3,4-dimethoxy)phenyl-1,3-dioxolo[4,5-g]quinoline,
6-(3,4-dihydroxy-5-methoxy)phenyl-1,3-dioxolo[4,5-g]quinoline,
6-(3,4-dimethoxy-5-hydroxy)phenyl-1,3-dioxolo[4,5-g]quinoline,
6-(3-benzyl-2,4-dihydroxy)phenyl-1,3-dioxolo[4,5-g]quinoline,
6-(2,4-dihydroxy)phenyl-1,3-dioxolo[4,5-g]quinoline or
6-[2,4-dihydroxy-3-(N,N-dimethylaminomethyl)]-phenyl-1,3-dioxolo[4,5-g]quinoline.

14. A method of claim 11 wherein said tumor is colon or rectal tumor.

15. A compound of formula (IA)

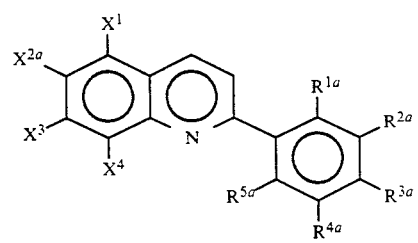

wherein:
$R^{1a}$ is hydrogen or protected hydroxy;
$R^{2a}$ is hydrogen, protected hydroxy, methoxy or methoxymethoxy;
$R^{3a}$ is hydrogen, protected hydroxy, protected amino, methoxy, methoxymethoxy or, taken together with $R^{2a}$, methylenedioxy;
$R^{4a}$ is hydrogen, protected hydroxy, methoxy, methoxymethoxy, benzyl, di($C_{1-4}$)alkylaminomethyl or, taken together with $R^{3a}$, methylenedioxy;
$R^{5a}$ is hydrogen or hydroxy; provided that at least one of $R^{1a}$ through $R^{5a}$ is other than hydrogen; and
$X^1$ taken together with $X^{2a}$, $X^{2a}$ taken together with $X^3$ or $X^3$ taken together with $X^4$, is methylenedioxy, provided that each of the remaining respective $X^1$, $X^{2a}$, $X^3$ and $X^4$ substituents are hydrogen.

16. A compound of claim 13 which is:
6-(4-methoxymethoxy)phenyl-1,3dioxolo[4,5-g]quinoline,
6-(3,4-dibenzyloxy-5-methoxy)phenyl-1,3-dioxolo[4,5-g]quinoline,
6-(3-benzyloxy-4,5-dimethoxy)phenyl-1,3-dioxolo[4,5-g]quinoline or
6-(2,4-dibenzyloxy)phenyl- 1,3-dioxolo[4,5-g]quinoline.

* * * * *